United States Patent [19]

Powell et al.

[11] Patent Number: 5,026,524
[45] Date of Patent: Jun. 25, 1991

[54] APPARATUS FOR SUBJECTING A LOAD TO A CONSTANT TEMPERATURE BELOW 100° C. IN A CLOSED CHAMBER

[75] Inventors: Anthony D. Powell, Lima; Raymond J. Miller, Penfield, both of N.Y.

[73] Assignee: MDT Corporation, Torrance, Calif.

[21] Appl. No.: 54,809

[22] Filed: May 27, 1987

Related U.S. Application Data

[63] Continuation-in-part of Ser. No. 901,230, Aug. 28, 1986, abandoned.

[51] Int. Cl.$^5$ ................................................ A61L 2/00
[52] U.S. Cl. ......................................... 422/26; 422/33; 422/108; 422/109; 422/110; 422/111; 422/112; 422/116
[58] Field of Search .................... 422/26, 33, 107, 108, 422/109, 110, 111, 116, 112

[56] References Cited

U.S. PATENT DOCUMENTS

| | | | |
|---|---|---|---|
| 3,450,487 | 6/1969 | Wallden | 422/26 |
| 4,238,447 | 12/1980 | Wolff | 422/26 |
| 4,239,731 | 12/1980 | Gillis et al. | 422/33 X |
| 4,395,383 | 7/1983 | Kackos | 422/33 X |

FOREIGN PATENT DOCUMENTS

887848  1/1962  United Kingdom .

Primary Examiner—David A. Simmons
Assistant Examiner—Thi Dang
Attorney, Agent, or Firm—Trask, Britt & Rossa

[57] ABSTRACT

Method and apparatus for providing a low temperature environment at a substantially constant and uniform temperature. A closed chamber is provided with an inlet and outlet. The chamber is operated at subatmospheric pressure. Steam is introduced into the chamber for providing the heating environment at a preselected temperature. A vacuum is applied to the chamber to regulate the steam about its saturation point for a preselected temperature.

22 Claims, 5 Drawing Sheets

APPARATUS FOR SUBJECTING A LOAD TO A CONSTANT TEMPERATURE BELOW 100° C. IN A CLOSED CHAMBER

This is a continuation-in-part of application Ser. No. 901,230, filed Aug. 28, 1986 now abandoned.

BACKGROUND OF THE INVENTION

This invention relates to an apparatus of the type used to subject culture media and/or instruments to temperatures below 100° C. for predetermined time periods, also referred to as low temperature sterilization.

An important aspect of providing low temperature sterilization is the maintaining of a substantially constant and uniform temperature within the chamber, preferably within plus or minus 0.5° C.

One method in the prior art for providing low temperature sterilization is described in U.S. Pat. No. 4,395,383. Such prior art devices waste large amounts of energy in the form of condensed steam which is continuously passed to drain. Additionally, this device requires numerous control and sensing mechanisms in order to get the chamber to its working temperature and maintaining at such temperature.

Applicants invention provides a simple, efficient and economical method and apparatus for providing a low temperature sterilizing apparatus.

SUMMARY OF THE INVENTION

Method and apparatus for providing a low temperature environment at a substantially constant and uniform target temperature. For the purpose of this invention, low temperature sterilization shall mean temperature below 100° C., preferably in the range of about 76° C to 99° C. A closed chamber is provided with an inlet, an outlet and a temperature sensor Steam is introduced into the chamber through the inlet for providing heat to bring the enviroment to the target temperature. The chamber is operated at subatmospheric pressure by intermittently applying a vacuum to the outlet to regulate the steam about its saturation point for the preselected target temperature.

The apparatus further includes control means which control the intermittent aplication of vacuum to the chamber. The vacuum is applied only as required to maintain the steam in a saturated condition. In one embodiment, the admission of steam and the application of vacuum are both controlled solely according to changes in the chamber temperature. In a second embodiment, the admission of steam is controlled according to chamber temperature, but the application of vacuum is controlled according to whether the steam in the chamber is in a saturated condition.

DETAILED DESCRIPTION OF THE INVENTION

Figure 1:
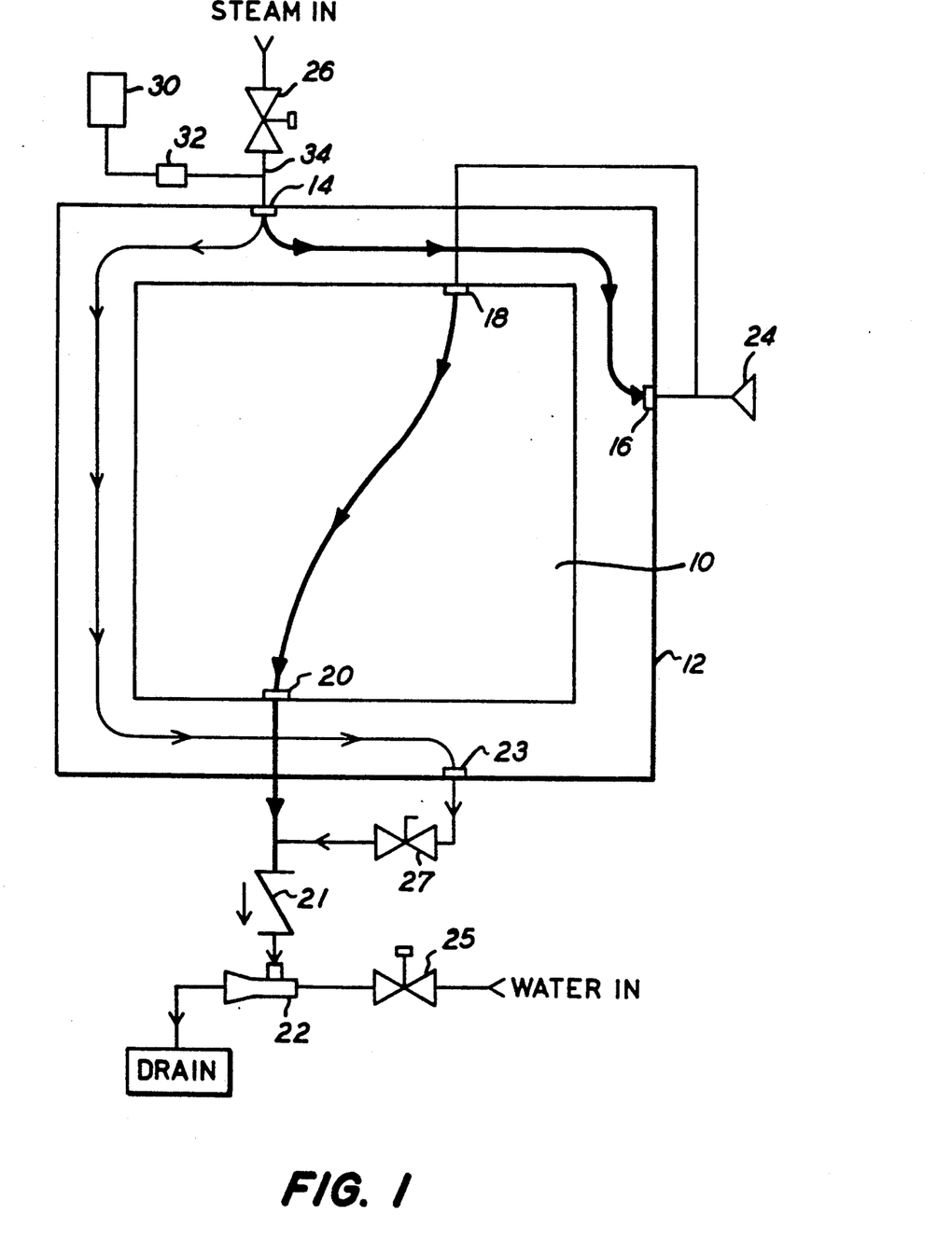
FIG. 1 is a schematic diagram of the preferred apparatus embodying the present invention.

FIG. 1 illustrates in schematic form an apparatus for use according to the present invention. A sterilizing chamber 10 is appropriately provided with a door (not shown) which may be opened to allow placement of articles therein. The door should be capable of providing an appropriate seal when closed. A jacket chamber 12 is provided which completely surrounds sterilization chamber 10. The jacket chamber 12 has an inlet 14 connected to a steam source which provides steam at a temperature greater than 100° C. and supra-atmospheric pressure. The jacket chamber 12 also has an outlet 16 which is connected by appropriate piping to the inlet 18 of chamber 10. Sterilization chamber 10 is provided with an outlet 20 which is connected to a water ejector 22 through check valve 21. The flow of water through ejector 22 is controlled by solenoid valve 25. When ejector 22 is operated a vacuum will be applied to outlet 20 which of course will provide a vacuum to chamber 10. A temperature sensor 24 is disposed in the jacket chamber 12 for monitoring the temperature of steam therein. The temperature of the steam in jacket chamber 12 is directly related to the temperature of the steam in chamber 10. Jacket chamber 12 has a second outlet 23 which is connected to ejector 22 through needle valve 27. The ejector 22 also applies a vacuum to jacket chamber 12 in the same manner as chamber 10. The condensed steam from chambers 10 and 12 along with the water used to operate ejector 22 goes to drain. Needle valve 27 is provided to restrict the flow through the jacket outlet 23 thereby allowing the great majority of the steam to flow through chamber 10.

In a preferred embodiment, a control means such as a microprocessor is constructed to control the water ejector 22 such that the ejector will not operate when steam is being admitted to the jacket chamber 12. Temperature sensor 24 is connected to the microprocessor which opens solenoid valve 26 so as to allow steam to enter into jacket chamber 12 when the temperature sensed to chamber 12 is below a lower boundary value. The microprocessor turns on the vacuum source when the temperature in the chamber rises above an upper boundary temperature for chamber 10. The vacuum source remains on until the steam in the chamber 10 reaches its saturation pressure point for the target temperature, after which as the ejector continues to operate the further reduction in chamber pressure leads to expansion and cooling of the steam therein. When the temperature sensed within the chamber falls below the lower boundary value, the ejector is deactivated and the steam value is again opened to admit steam to the chamber.

Therefore, when steam is flowing into the jacket chamber 12, water flow to the ejector is shut off and when steam is shut off, water will flow through the ejector 22 thereby pulling a vacuum on sterilizer chamber 10 and jacket chamber 12. The control means so constructed brings steam within the chamber to its saturation pressure for a preselected target temperature which falls between the upper and lower boundary values, and maintains the steam in that condition, without any requirement for monitoring the chamber pressure.

When the apparatus is started from a cold start, steam is injected into the jacket chamber 12. The steam condenses and the air and water are discharged through needle valve 27. When the temperature sensor senses that the steam in jacket chamber 12 has reached the upper boundary value, the microprocessor will shut off the steam supply by closing solenoid valve 26 and the ejector 22 will be activated by opening valve 25 thereby drawing off condensate and lowering the temperature and pressure of the steam within the sterilization chamber 10 and jacket chamber 12. The lower pressure causes the steam in the chambers 10 and 12 to expand, thus lowering the temperature. The temperature sensor 24 senses this lower temperature. When the temperature in the jacket chamber 12, drops below the preselected temperature, the microprocessor deactivator the ejector and reopens solenoid 26 allowing additional steam to enter. This process is repeated until the sterilization chamber 16 and jacket chamber 12 are warmed up to the preselected working temperature. During the initial warm up stage, the ejector will be running substantially longer than the steam flowing into the chambers 10 and 12. Once the operating temperature in chamber 10 is achieved the alternate steam and ejector cycles continue, but the amount of time the ejector is operated and the time period the steam is allowed to enter chambers 10 and 12 is preferably kept substantially the same. Applicants have found that in order to obtain this substantially equal balance, the solenoid 26 has a 3/32 inch (2.38 mm) orifice and the ejector 22 is designed to evacute 100 cubic foot tank to 15 inches of Mercury absolute (Hg. Abs.) in 74 minutes. The process of allowing steam into chamber 10 and applying a vacuum to chamber 10 will continue for as long as has been programmed in the microprocessor for the desired preselected temperature.

The present invention requires only to monitor a single temperature which can be easily done by a single temperature sensor. This allows ease in selecting different operating temperatures to be controlled. Additionally, the controlling of steam and vacuum is a function of a single parameter. Regulating the steam about its saturation point effect uniformity of temperatures throughout the chamber 10, minimizing the danger of overheating the contents. Alternating the entrance of steam into chamber 10 and applying a vacuum to chamber 10 minimizes the amount of energy (heat loss) that goes to drain.

In the preferred embodiment a small amount of air is introduced into chamber 10. In the particular embodiment illustrated air is introduced into the steam line going to inlet 14. Air enters filter 30 through orifice 32 to steam line 34. Orifice 32 allows only a very small amount of air to enter. Applicants have found that an orifice having a diameter of about 5.08 mm (0.02 inches) is adequate.

The apparatus of FIG. 1 has been found to maintain the temperature in a chamber 10 size 20"×20"×28" to within ±0.5° C. of the target temperature. Steam was imtroduced into jacket chamber 12 at a temperature of 150° C. and pressure of 60 psi. An operating temperature of 80° C. was selected. The temperature sensor 24 in jacket chamber 12 sends the appropriate information to the microprocessor. The microprocessor was programmed so that when a temperature below of 80° C. was sensed in chamber 10, valve 26 was opened allowing steam to enter jacket chamber 12. In the particular apparatus used there was about a two degree difference between the temperature in chamber 10 and the temperature sensed by temperature sensor 24 in jacket chamber 12. Therefore, the temperature sensor 24 measured 82° C. when the temperature in chamber 10 was 80° C. The microprocessor was programmed accordingly. When the temperature sensor 24 measured a temperature of 83° C., the valve 26 was closed and valve 25 was opened thereby applying a vacuum to chamber 10. The apparatus then cycled between allowing steam to enter and applying a vacuum. Once the chamber 10 reached the preselected operating temperature, the cycle time for allowing steam to enter and applying a vacuum was more equal. In the embodiment illustrated the steam cycle was about two (2) seconds and the vacuum cycle was about four (4) seconds.

Figure 2:
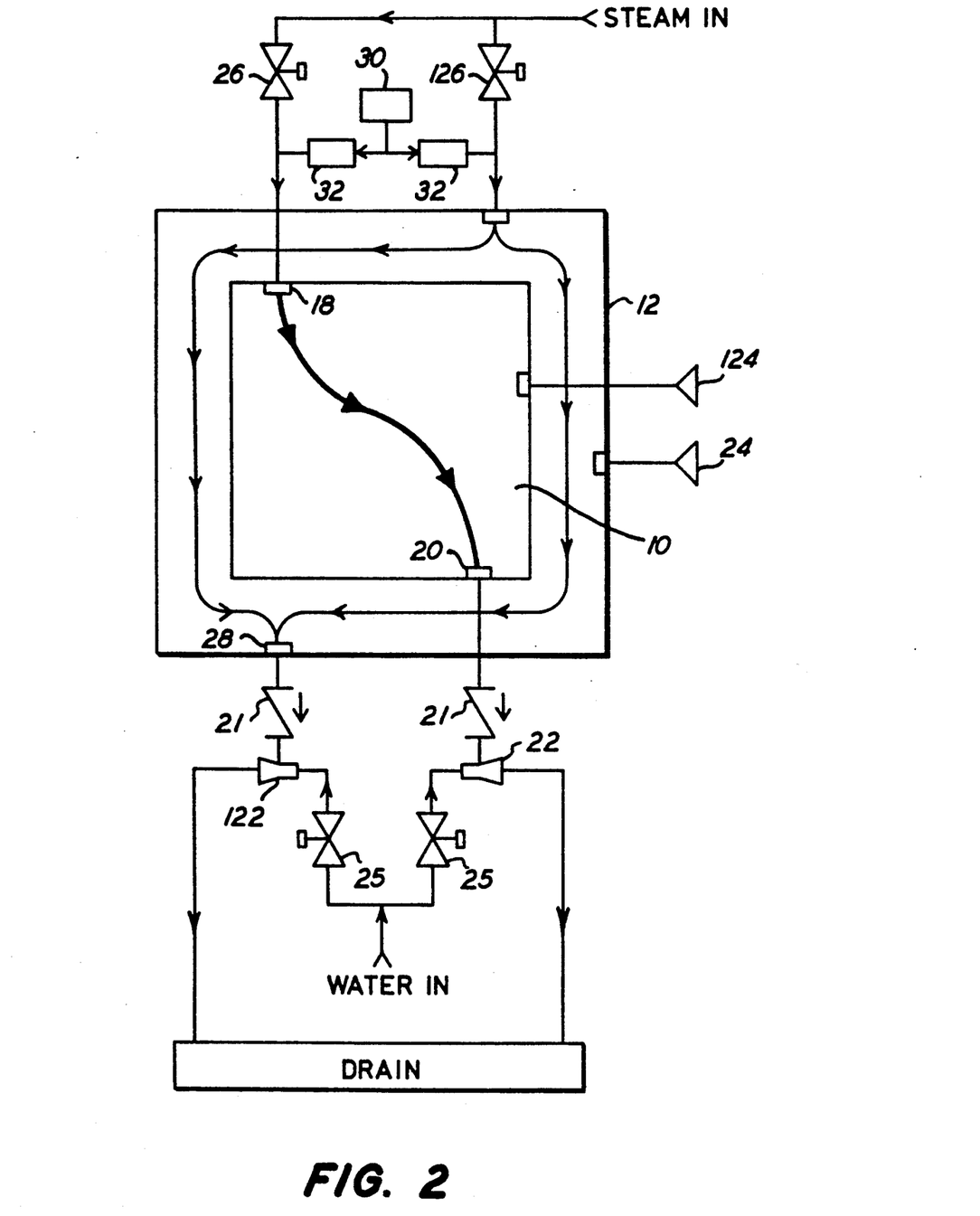
FIG. 2 is a schematic diagram of a modified apparatus embodying the present invention.

FIGS. 2, 3, 4, 5 and 6 illustrate various modified forms of the present invention, identical numerals indicating like parts. Referring to FIG. 2 there is illustrated an embodiment similar to FIG. 1 except that instead of steam entering into chamber 10 from jacket chamber 12, the steam enters directly into inlet 18 of chamber 10 and directly into jacket chamber 12 through a second solenoid 126. Additionally, a second temperature sensor 124 is provided in chamber 10 and is appropriately connected to the microprocessor. The jacket chamber 12 has only a single outlet 28 connected to a separate ejector 122 and the sterilization chamber 10 is connected to its own ejector 22 through outlet 20. This particular embodiment operates substantially identical as the apparatus of FIG. 1 except the jacket chamber 12 and sterilization chamber 10 operates independently of each other so that each may operate its own preselected temperature.

Figure 3:
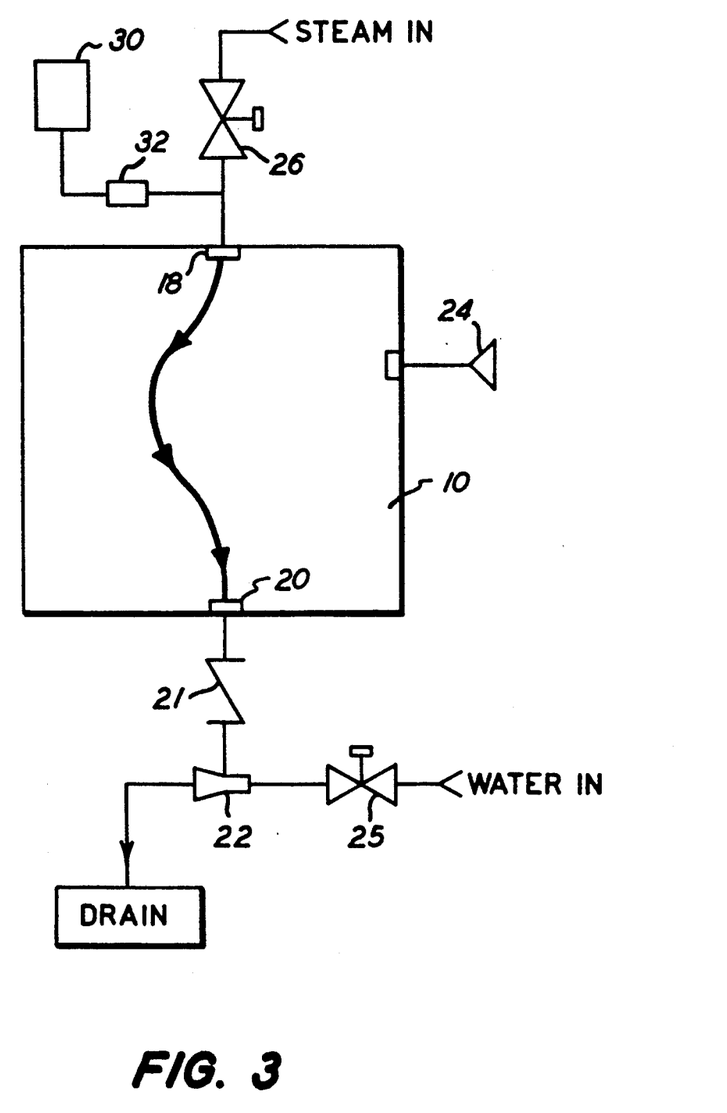
FIG. 3 is a schematic diagram of yet another embodiment of the apparatus made in accordance with the present invention.

FIG. 3 is an embodiment similar to that illustrated in FIG. 1 except the jacket chamber 12 is omitted and the temperature sensor 24 is placed in the sterilization chamber 10. In this embodiment, it is recommended that the outer surface of sterilization chamber be adequately insulated. This embodiment also operates in the same manner as the apparatus of FIG. 1.

Figure 4:
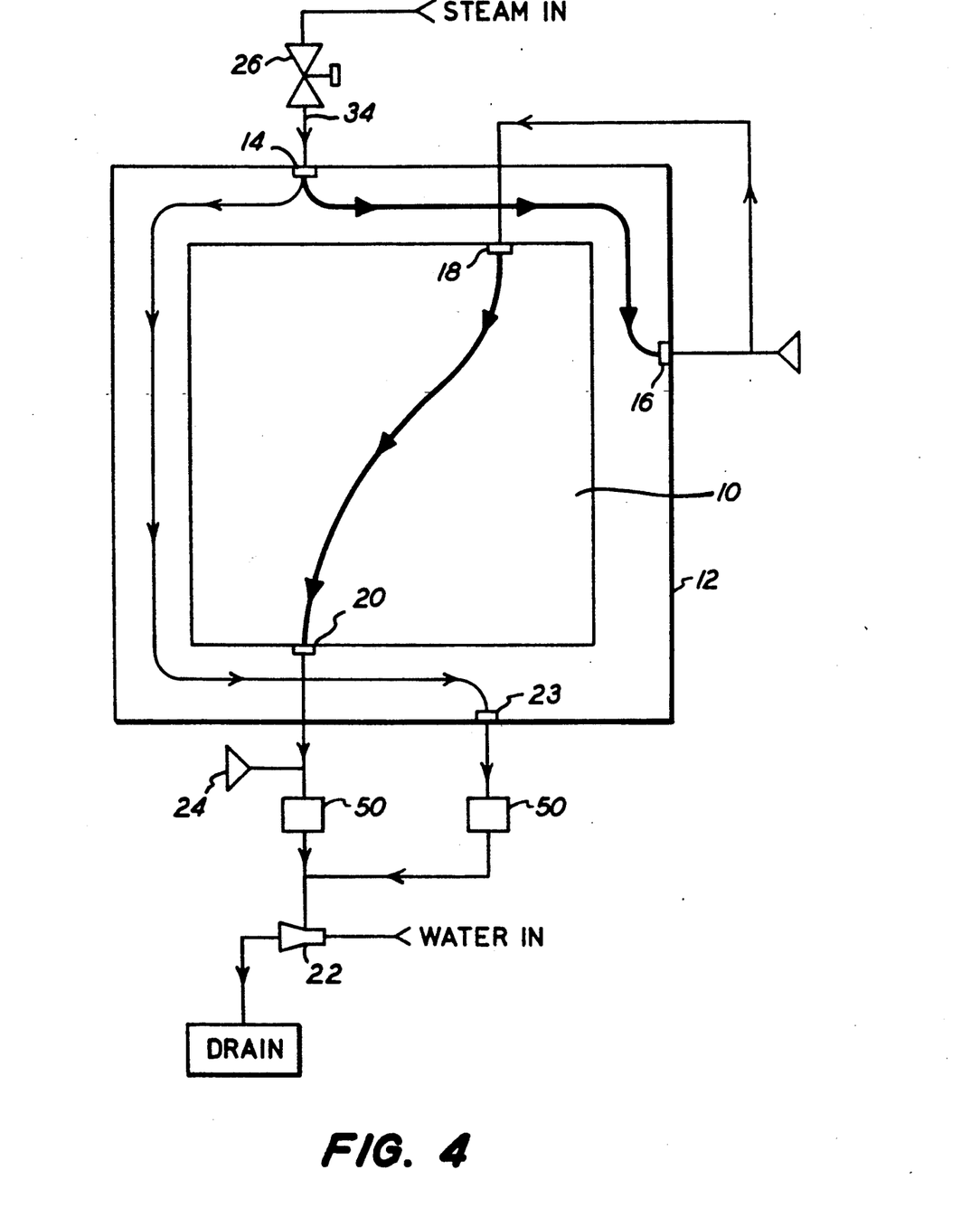
FIG. 4 is a schematic diagram of yet still another apparatus made in accordance with the present invention.

Referring to FIG. 4 there is illustrated an alternate preferred embodiments of the present invention similar to that of FIG. 1. As in the embodiment of FIG. 1, the microprocessor admits steam into the jacket chamber 12 and sterilization chamber 10 when the temperature falls below the preset lower boundary value. However, the control means governing the application of vacuum to chambers 10 and 12 is steam traps 50 connected to the outlets 20 and 23, instead of a microprocessor. The steam traps 50 of the embodiment illustrated are thermostatic pressure balanced thermostatic traps which closely follow the steam saturation curve. From a cold start, steam is injected into the jacket chamber and condenses. As the chamber 10 warms up, the traps 50 remain open due to the condensate going through them. The open traps 50 allow the ejector 22 to lower the pressure in chambers 10 and 12 which lowers the saturation temperature of the steam. When the temperature in the chamber reaches the preset upper boundary value, the microprocessor turns off the steam. The traps stay open, allowing evacuation of the chamber for as long as condensation continues to occur, i.e. until the pressure in chambers 10 and 12 is reduced to the saturation point for the preset temperature. When the pressure reaches that point, condensation ceases and the traps close, holding the pressure substantially constant.

Eventually the temperature drops below the lower boundary value, triggering the admission of steam to the chambers. The resultant increase in pressure and temperature leads to condensation of the steam, which in turn causes the traps to open, repeating the cycle. In this particular embodiment temperature sensor 24 measures the temperature of the drain as is normally done in sterilization.

Figures 5, 6:
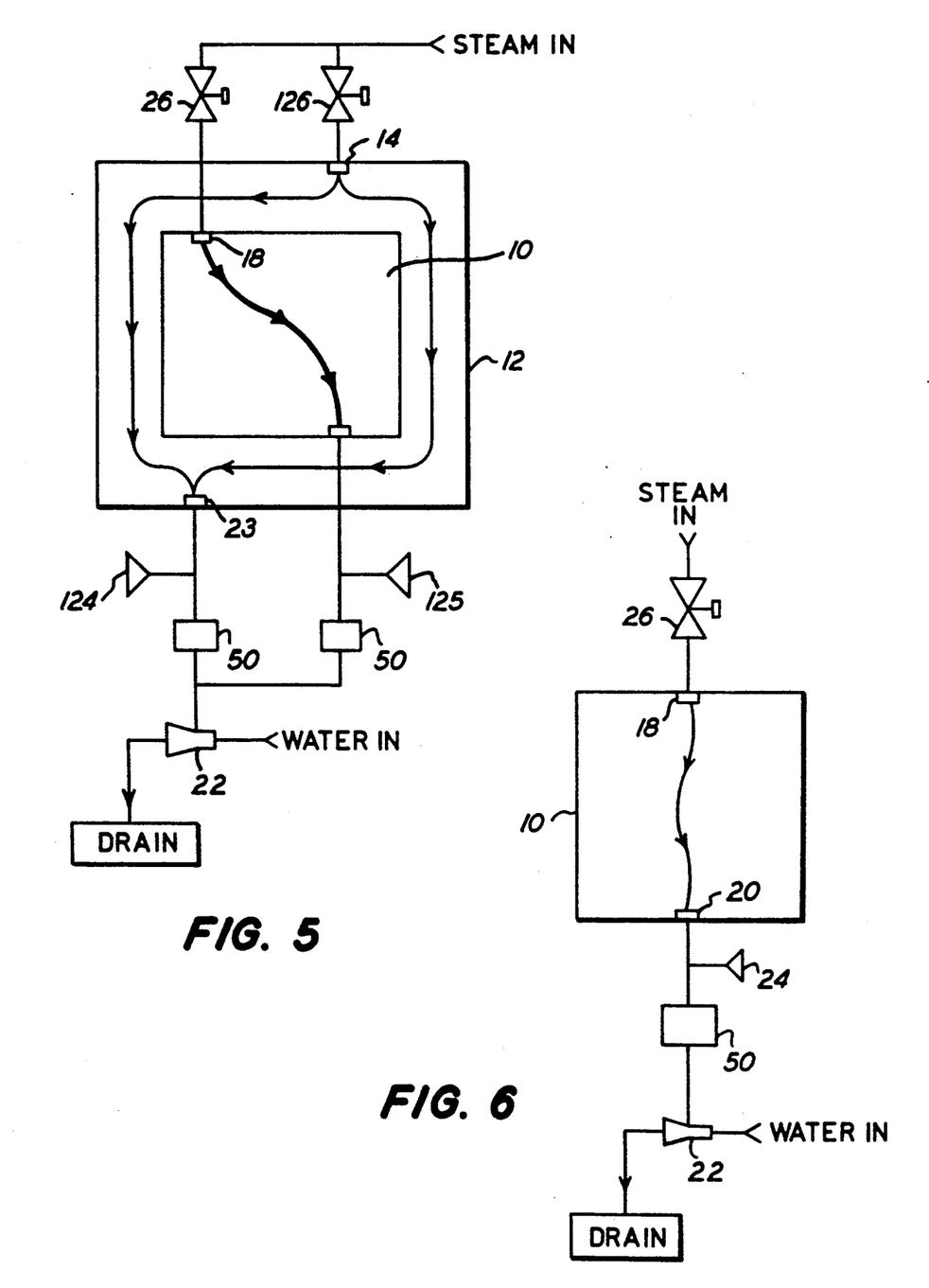
FIG. 5 is a schematic diagram of a further embodiment of an apparatus according to the present invention.
FIG. 6 is a schematic diagram of another embodiment of the apparatus made in accordance with the present invention.

The embodiment of FIG. 5 operates in the same manner as the apparatus in FIG. 4 however as in FIG. 2 chamber 10 is independently connected to the steam source. The steam traps as in FIG. 4 are used to determine when the vacuum is to be applied to the sterilization chamber 10 and jacket chamber 12. Additionally in this embodiment, as in FIG. 2, the chamber and jacket chambers may be kept at different preselected temperatures.

The embodiment illustrated in FIG. 6 also uses a steam trap for controlling the vacuum applied to the chamber 10, however, the jacket chamber 12 is omitted as in FIG. 3.

While the present invention has been described with regard to the particular embodiments illustrated, various modifications may be made without departing from the scope of the present invention.

What is claimed is:

1. An apparatus for sterilizing a load at substantially constant and uniform temperature below 100° C. within a closed sterilization chamber connected through an inlet to a steam source and through an outlet to a vacuum source, said apparatus comprising:
   steam valve means operably associated with said inlet for regulating the flow of steam from the steam source to the interior of said chamber through the inlet;
   temperature sensor means positioned for sensing the temperature in the interior of said chamber and operable to generate signals corresponding to said temperature; and
   control means for controlling the admission of steam to said chamber and the evacuation of said chamber by said vacuum source, thereby maintaining the temperature within said chamber between a preset lower boundary value and a preset upper boundary value, including
      steam flow control means connected to said temperature sensor and said steam valve means to receive signals from said sensor means and in response to said signals selectively to operate said steam valve means to admit steam to said chamber interior when the temperature sensed by said sensor means is below said lower boundary value and to prevent admission of steam to the chamber when the temperature sensed by said sensor means exceeds said upper boundary value, and
      evacuation control means responsive to a condition of steam within said chamber and operably associated with said outlet and said vacuum source for evacuating the interior of said chamber during sterilization, said evacuation control means operable to intermittently evacuate said chamber through said outlet in response to a particular steam condition sensed within said chamber.

2. The apparatus of claim 1 wherein said evacuation control means includes vacuum operation means operably connected to said vacuum source and said temperature sensor means for receiving signals from said sensor means and for operating said vacuum source in response to said signals to evacuate said chamber when the temperature sensed by said sensor means exceeds said upper boundary value and to prevent evacuation of said chamber when the temperature sensed by said sensor means is below said lower boundary value.

3. The apparatus of claim 1, wherein said evacuation control means includes condensate responsive control means operably associated with said vacuum source and said outlet for sensing the presence and absence of condensed steam within said chamber and in response thereto selectively connecting said vacuum source to evacuate said chamber when condensed steam is sensed therein and disconnecting said vacuum source when condensed steam is not sensed in said chamber.

4. The apparatus of claim 3 wherein said condensate responsive control means is a steam trap.

5. An apparatus for sterilizing a load at substantially constant and uniform temperature below 100° C. within a closed sterilization chamber connected through an inlet to a steam source and through an outlet to a vacuum source, said apparatus comprising:
   steam valve means operably associated with said inlet for regulating the flow of stream from the steam source to the interior of said chamber through the inlet;
   evacuation control means operably associated with said outlet and said vacuum source for intermittently connecting said vacuum source to evacuate the interior of said chamber through said outlet;
   temperature sensor means positioned for sensing the temperature in the interior of said chamber and operable to generate signals corresponding to said temperature; and
   control means connected to said steam valve means, evacuation control means and temperature sensor means for receiving signals from said sensor means and for operating said steam valve means in response to said signals to admit steam to said chamber interior when the temperature sensed by said sensor means is below a preset lower boundary value and to prevent the admission of steam to the chamber interior when the temperature sensed by said sensor means exceeds a preset upper boundary value, said control means being further operable to activate said evacuation control means in response to said signals to evacuate the interior of said chamber when the temperature sensed by said sensor means exceeds said upper boundary value and to prevent evacuation of said chamber interior when the temperature sensed by said sensor means is below said lower boundary value.

6. The apparatus of claim 5, wherein the dimensions of said steam valve means governing the rate of steam admission from said steam source and the rate of evacuation by said vacuum source are coordinately selected to provide periods of steam admission to the chamber which are substantially similar in duration to the time periods during which vacuum is applied.

7. The apparatus of claim 5 including a jacket chamber which surrounds said sterilization chamber and which is connected through an inlet to said steam source and through an outlet to said vacuum source.

8. The apparatus of claim 7, wherein said control means is a microprocessor.

9. The apparatus of claim 8, further including means for admitting air to the interior of said sterilization chamber operably associated with said inlet.

10. An apparatus for providing a saturated steam environment at substantially constant and uniform temperature below 100° C. within a closed sterilization chamber connected through an inlet to a steam source and through an outlet to a vacuum source, said apparatus comprising:

steam valve means operably associated with said inlet for regulating the flow of steam from the steam source to the interior of said chamber through the inlet;

temperature sensor means positioned for sensing the temperature in the interior of said chamber and operable to generate signals corresponding to said temperature; and control means operatively disposed for coordinating the admission of steam to said chamber and the application of vacuum to said chamber thereby to maintaim the chamber interior at a substantially constant temperature, said control means including:

steam flow control means operably connected to said temperature sensor and said steam valve means to receive signals from said sensor means and in response to said signals to operate said steam flow control means to admit steam to said interior when the temperature sensed by said sensor means is below a preset lower boundary value and to prevent the admission of steam to the chamber when the temperature sensed by said sensor means exceeds a preset upper boundary value, condensate responsive control means operably associated with said vacuum source and said outlet for sensing the presence and absence of condensed steam within said chamber and in response thereto connecting said vacuum source to evacuate said chamber when condensed steam is sensed therein and disconnecting said vacuum source when condensed steam is not sensed in said chamber.

11. The apparatus of claim 10, in which said condensate responsive control means is a steam trap.

12. The apparatus of claim 11, in which the dimensions of said steam valve means governing the rate of steam admission from said steam source and the rate of evacuation by said vacuum source are coordinately selected to provide periods during which steam is admitted which are substantially similar in duration to the periods during which vacuum is applied.

13. The apparatus of claim 11, including a jacket chamber which surrounds said sterilization chamber and which is connected through an inlet to said steam source and through an outlet to said vacuum source.

14. The apparatus of claim 13, further including means for admitting a small amount of air to the interior of said sterilization chamber operably associated with said inlet.

15. A method for sterilizing a load at substantially constant and uniform temperature below 100° C. within a closed sterilization chamber connected through an inlet to steam source and through an outlet to a vacuum source, said apparatus having steam valve means operably associated with said inlet for regulating the flow of steam from the steam source to the interior of said chamber through the inlet, vacuum operation means operably associated with said outlet for intermittently connecting said vacuum source to evacuate the interior of said chamber through said outlet, and temperature sensor means positioned for sensing the temperature in the interior of said chamber and operable to generate signals corresponding to said temperature, said method comprising the steps of:

opening said steam valve means to admit steam to the chamber when the temperature sensed by said sensor means is below a lower boundary value;

closing said steam valve means preventing steam from entering said chamber when the temperature sensed by said sensor means exceeds an upper boundary value;

connecting said vacuum source during sterilization to evacuate the interior of said chamber when the temperature sensed by said sensor means exceeds said upper boundary value; and disconnecting said vacuum source when the temperature sensed by said sensor means is below said lower boundary value.

16. The method of claim 15, wherein the periods during which the chamber is evacuated are substantially equal in duration periods during which steam is admitted to the chamber, and where alternation between these two periods is frequent.

17. The method of claim 16, where a small amount of air is admitted to the chamber through said inlet.

18. A method for operating an apparatus to provide a saturated steam enviroment at substantially constant and uniform temperature below 100° C. within a closed sterilization chamber connected through an inlet to a steam source and through an outlet to a vacuum source, said apparatus having steam valve means operably associated with said inlet for regulating the flow of steam from the steam source to the interior of said chamber through the inlet and temperature sensor means positioned for sensing the temperature in the interior of said chamber and operable to generate signals corresponding to said temperature, said apparatus further having a condensate responsive control means operably associated with said outlet and said vacuum source for opening said chamber to said vacuum source when condensate is present in said chamber and closing said chamber to said vacuum source when condensate is absent from said chamber, said method comprising the steps of:

opening said steam valve means to admit steam to the chamber when the temperature sensed by said sensor means is below a lower boundary value; and closing said steam valve means preventing steam from entering said chamber when the temperature sensed by said sensor means exceeds an upper boundary value.

19. In an apparatus for sterilizing a load at substantially constant and uniform temperature below 100° C. within a closed sterilization chamber connected through an inlet to a steam source and through an outlet to a vacuum source, said apparatus having steam flow control means operably associated with said inlet for regulating the flow of steam from the steam source to the interior of said chamber through the inlet, temperature sensor means positioned for sensing the temperature in the interior of said chamber and operable to generate signals corresponding to said temperature, steam circuit means operably associated with said steam flow control means and said temperature means for receiving signals from said sensor means and in response to said signals operating said steam flow control means to admit steam to the chamber when the temperature sensed therein is below a preset lower boundary value and to prevent admission of steam to the chamber when the temperature therein exceeds a preset upper boundary value, an improved vacuum control device comprising:

evacuation control means responsive to a condition of steam within said chamber and operably associated with said outlet and said vacuum source for intermittently evacuating the interior of said chamber during sterilization in response to the particular steam condition sensed within said chamber thereby maintaining the temperature within said chamber interior between said upper and lower boundary values.

20. The improved device of claim 19 in which said evacuation control means comprises:

vacuum control means operably associated with said outlet and said vacuum source for intermittently connecting said vacuum source to evacuate the interior of said chamber through said outlet; and vacuum circuit means operably associated with said temperature sensor means and said vacuum control means for receiving signals from said sensor means and operable to activate said vacuum control means in response to said signals to connect said vacuum source to the interior of said chamber when the temperature sensed by said sensor means exceeds said upper boundary value and to disconnect said vacuum source when the temperature sensed by said sensor means is below said lower boundary value.

21. The improved apparatus of claim 19, in which said evacuation control means includes:

condensate responsive control means operably associated with said vacuum source and said outlet for sensing the presence and absence of condensed steam within said chamber and in response thereto connecting said vacuum source to evacuate said chamber when condensed steam is sensed therein and disconnecting said vacuum source when condensed steam is not sensed in said chamber.

22. The improved device of claim 21, in which said condensate responsive control means is a steam trap.

* * * * *